(12) United States Patent
Dirla et al.

(10) Patent No.: US 8,107,066 B2
(45) Date of Patent: Jan. 31, 2012

(54) TRAY-SHAPED CONTAINER FOR TEST OBJECTS TO BE OPTICALLY ANALYZED AND PRODUCT DEVICE THEREFORE

(75) Inventors: Felix Dirla, Frankfurt a.M. (DE); Robert Jaeger, Hofheim/Ts. (DE)

(73) Assignee: Bioscitec GmbH, Frankfurt am Main (DE)

( * ) Notice: Subject to any disclaimer, the term of this patent is extended or adjusted under 35 U.S.C. 154(b) by 249 days.

(21) Appl. No.: 12/228,083

(22) Filed: Aug. 14, 2008

(65) Prior Publication Data
US 2009/0284738 A1 Nov. 19, 2009

(30) Foreign Application Priority Data
Oct. 24, 2007 (DE) .................... 20 2007 014 923 U

(51) Int. Cl.
*G01N 21/01* (2006.01)
(52) U.S. Cl. ....................................................... 356/244
(58) Field of Classification Search .................... None
See application file for complete search history.

(56) References Cited

U.S. PATENT DOCUMENTS

| 5,418,136 A | 5/1995 | Miller et al. |
| 5,772,967 A * | 6/1998 | Wannlund et al. ............ 422/102 |
| 6,531,702 B1 | 3/2003 | Mischler et al. |
| 2004/0107986 A1 * | 6/2004 | Neilson et al. ................. 136/204 |

FOREIGN PATENT DOCUMENTS

| DE | 19815943 A1 | 10/1999 |
| EP | 0646784 | 4/1995 |
| EP | 1055457 A2 | 11/2000 |
| WO | 8807202 A1 | 9/1988 |
| WO | 9612940 | 5/1996 |

* cited by examiner

*Primary Examiner* — Tu Nguyen
(74) *Attorney, Agent, or Firm* — Perkins Coie LLP; Aaron Wininger

(57) ABSTRACT

A tray-shaped container comprising at least one cavity or recess for receiving the particular test objects, wherein these at least one recess comprises structured inner surfaces. Through this, a considerable reduction or even full reduction of interfering reflections and other optical irritations is achieved. In particular, the container constitutes an incubation tray for test stripes, having several longitude extending recesses. The inner surfaces of the recesses preferably comprise a grove-shaped and/or stair-shaped structure. The tray-shaped container may constitute an incubation tray for test stripes which are used in medical diagnostics.

15 Claims, 4 Drawing Sheets

TRAY-SHAPED CONTAINER FOR TEST OBJECTS TO BE OPTICALLY ANALYZED AND PRODUCT DEVICE THEREFORE

This application claims priority of German patent application no. 20 2007 014 923.9 filed Oct. 24, 2007.

FIELD OF THE INVENTION

The invention relates to a tray-shaped container for test objects to be optically illuminated, and particular to an incubation tray for test strips which are used in medical diagnostics. Moreover, the invention relates to a production device for deep-drawing of such a tray-shaped container out of thermoplastic material.

BACKGROUND

In medical diagnostics as well as generally in laboratory analysis, there are different types of test objects to be optically inspected under light, in particular test strips which are incubated in tray-shaped containers. The visual inspection of these test strips allows for example the conclusion of the current medical status of the check-upped patient.

It is quite often the case that the results and tests of medical diagnostics are still evaluated simply with the naked eye. For this purpose, the test objects are examined in the containers which are also referred to as incubation trays. Such a pure visual evaluation may only be performed reliably by skilled persons, such as physicians and trained staff, since only visual reactions in color of the test strips give direct information about allergy, drug abuse or infections.

Typically, the test objects or test strips to be analyzed comprise a certain pattern of reaction with many lighter or darked bands thereon, which represent a clear indicator for a particular disease, because of their intensity and their pattern. As an example, comparison strips or master patterns which are compared with the color reaction of test strips from the patients, can clearly give information about the presence and the status of a disease, such as borreliosis being passed by tics. However, beside the imperfect comparability of a pure visual diagnostics, the effort for the evaluation and the subsequent filing of the results, is very high. In particular, all test strips having the appearing color reactions must be stored in the dark because of their photo sensitivity. The filing or archiving is necessary on the other hand to allow a later validation of the test results.

SUMMARY

It is therefore desirable to have an automated evaluation of such test objects or test strips to be optically analyzed, wherein a failure-free picture generation can be achieved beside the incubation.

Because of this and for the purpose of standardization, as well as of enhancing the efficiency there are semi-automated methods or software-based systems for analyzing test strips which are increasingly used. Since these systems and methods always need to have, as possible, a failure-free and preferably digital picture image of the test strips to perform a reliable evaluation, it depends in particular on the quality of the picture generation. For this, test strips are usually illuminated by different methods or by one or several light sources to generate a digital picture by photo electronic devices.

Because of long-time experience in the field of quantification of scientific color reactions in science, the applicant developed a software supported sampling method (scanning) for automated analysis of diagnostic test strips, the method being of use in particular in diagnostics as a matter of routine. For this diagnostics, it is desirable that it is no longer necessary to take the test strips out of the particular incubation-tray by hand and to put them on the scanner, but leave them in the incubation-tray to be read out therein and to be scanned.

The present invention is based on the conclusion that a high contrast between test strips and incubation-tray within the generated picture is important for the subsequent picture or image processing.

It is object of the present invention to present inter alia a more enhanced tray-shaped container, in particular an incubation-tray for test strips which allows a considerably better image processing of the test objects to be optically illuminated and evaluated.

Further, a production device for the deep-drawing of such an tray-shaped container from thermo-plastic material shall be presented here.

Accordingly, a tray-shaped container is presented, comprising at least one cavity or recess for receiving the particular test objects, wherein at least one recess comprises structured inner surfaces. Through this, a considerable reduction or even full reduction of interfering reflections and other optical irritations is achieved.

In particular, the container constitutes an incubation tray for test strips, having several longitude extending recesses. The recesses are preferably tapered or cone-shaped, wherein each recess is expanded from the bottom to its opening. This tapered shaping may comprise straight or curved walls and is preferable only slightly shaped (precipitous walls). It is advantageous if the inner surfaces of the recesses comprise a grove-shaped and/or stair-shaped structure. The tray-shaped container may also be shaped such that the particular recess is not consistently tapered or cone-shaped, but expands from its bottom with an increasing pitch or sloop up to its opening. For example, the tapered shaping may be shaped more flat in the lower part of the recess than in the upper part.

Further, there is introduced a production or manufacturing device for deep-drawing or thermo-forming of such tray-shaped containers out of thermoplastic material, wherein the device comprised a positive form or profile and a negative form with groove shaped and/or stair shaped structure. Since both forms or profiles have structures which are adapted to each other and are corresponding to the desired profiling of the recess, a perfect result can be achieved by the thermo-forming of the plastics (plastic film or thin slide).

BRIEF DESCRIPTION OF THE DRAWINGS

In the following, the invention will be described by an embodiment of an incubation-tray. Thereby reference is made to the schematic drawings which represent the following.

DETAILED DESCRIPTION

Figure 1:
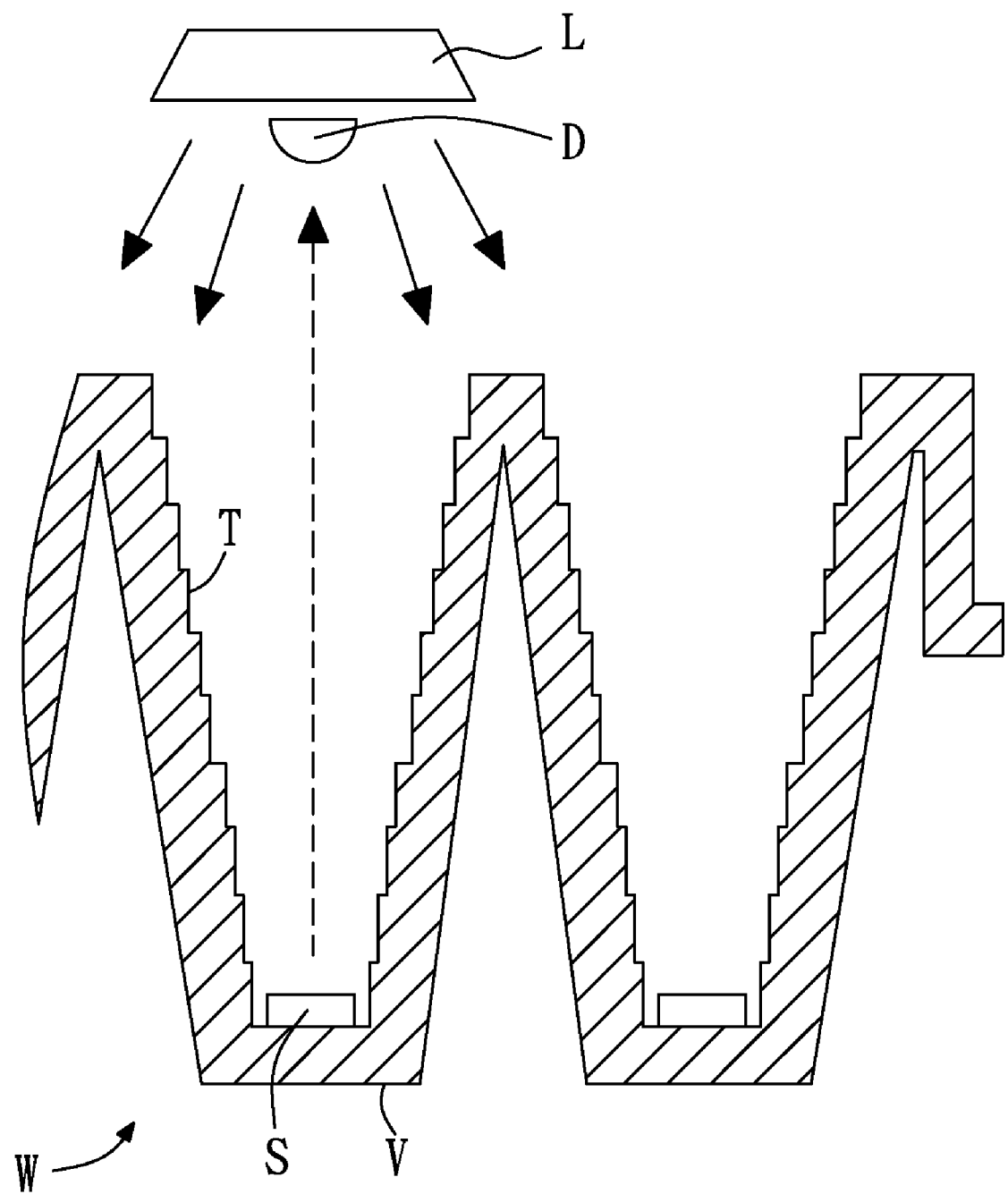
FIG. 1 shows in a sectional view the structure of a container according to the invention, having the shape of an incubation-tray with groove-shaped structure.

The FIG. 1 shows in a sectional view a container W, being designed as an incubation-tray, having several recesses W whose inner surface F comprises a grove-shaped or stair-shaped structure. The incubation-tray W, in the following also referred to as tray, comprises for example 50 recesses being arranged adjacent to each other and extending in longitude direction, wherein the recesses are designed as V-shaped grooves. The tray W consists of deep-drawn plastics, preferable of black-colored polystyrene and is used in form of a tray or storage box, made of 50 recesses being shaped in parallel.

FIG. 1 shows, as an example, a section of tray W with two adjacent recesses V, each being 1 cm deep. The tray W can receive in each of its recesses V a test strip S and allows thereby the analysis and the verification of disease of 50 patients. In order to scan several trays with test strips accommodated therein, the applicant has developed a scanner or a scanning system in which the test strips laying in the trays are digitally detected and analysed. The system may process a semi-automatic evaluation of the test strips as well as provide proposals of diagnostics to the physician. In FIG. 1, the system is represented for simplification by one light source L and by a detector of scanner D.

For optical analysis and picture processing, a high depth of field or focus shall be achieved to exactly detect the test strips a in the particular tray W. Because of the complex set of problems of a perfect illumination, it occurs in conventional trays that the test strips are reflected at the walls of the recesses and thus generate fictive pictures. Furthermore, it may happen that the light source may be reflected irregularly at the bottom of the recess and that in the worst case these reflections generate fictive extensions of test strips.

Figure 3B:
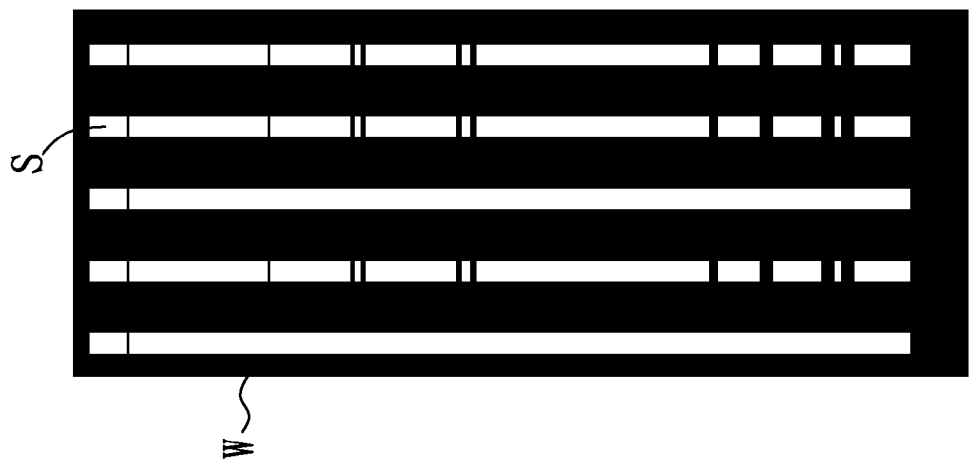
FIG. 3a/b shows in comparison photographs of test strips in a conventional incubation-tray and in an Incubation-tray being formed according to the invention (and shown in FIG. 1), and FIG. 4a/b/c shows in different views the dimension and the tapered shaping of the particular recess.
Figure 3A:
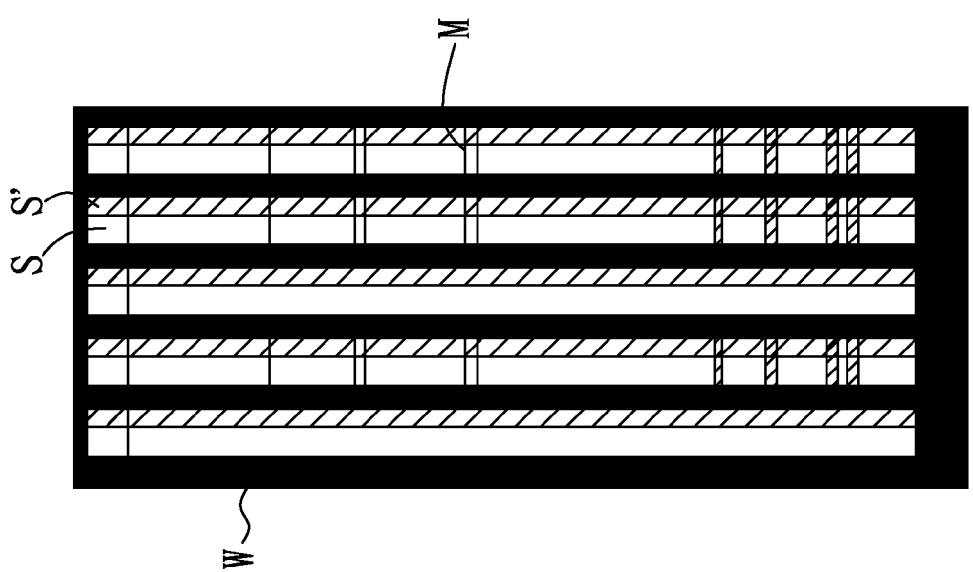

FIG. 3a illustrates this first negative effect, which occurs in conventional trays. FIG. 3b shows in comparison to this the considerably enhanced situation which can be achieved by the tray W, being structure on its inner surface, according to the invention (see FIG. 1). Therefore reference is made to both FIGS. 3a and 3b as well as to FIG. 1 in the following.

As shown in FIG. 3a, not only the real test strips S there are displayed when using a conventional tray, but also one or more simulacrum or fictive picture S' or fictive test strips S'. These "ghost strips" mainly occur at one side of the tray's edge. The applicant found out that these negative effects are dependent on the side of illumination and the position of the light-source L and that such "ghost strips" are classified mistakenly by an evaluation software to be real test strips and thus being evaluated and analysed.

By use of a container, such as the tray W shown in FIG. 1, the situation illustrated by FIG. 3b results in a considerable enhanced photograph. Now no more "ghost strips" occur, so that the quality of evaluation is considerably increased.

Figure 2:
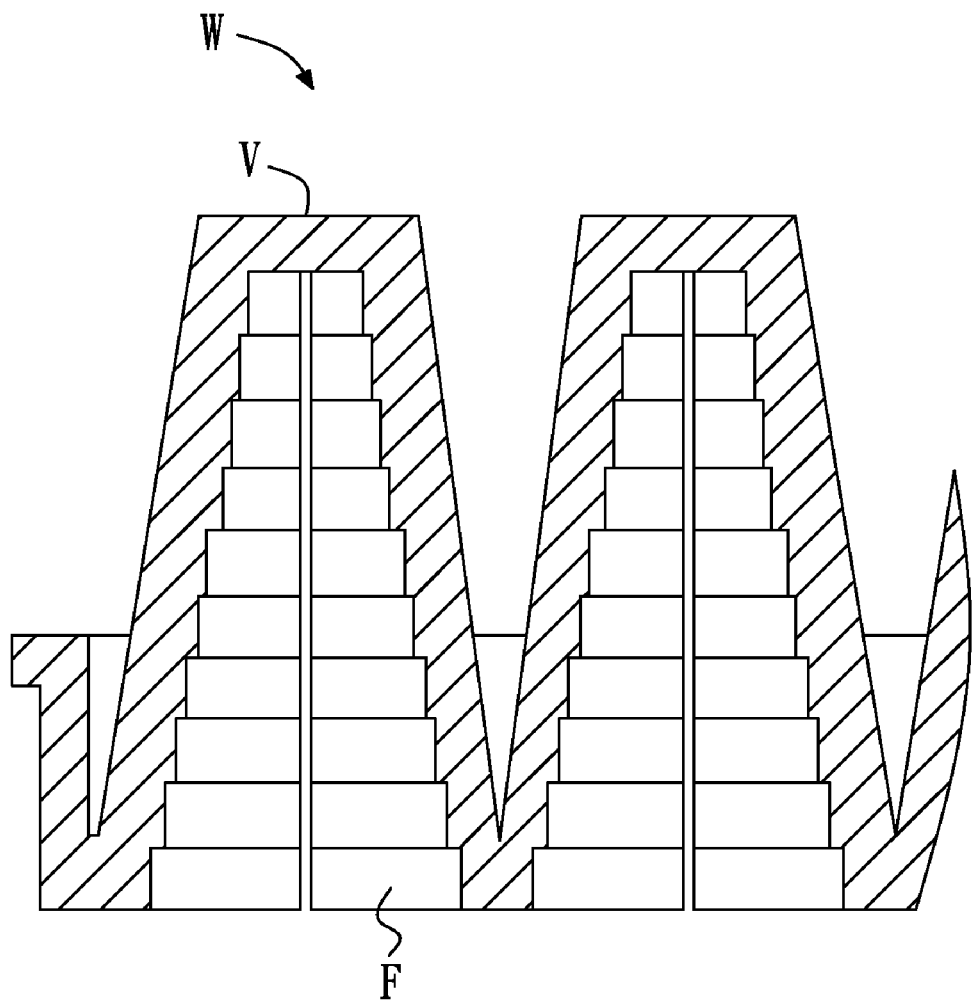
FIG. 2 illustrates the function of the production device for deep-drawing of such an incubation-tray, made of plastics.

When shaping the new tray W, it appeared that the grove-shaped or stair-shaped structure is in particular applicable, wherein the structure of the inner surface F comprises a first border edge K1, being directed to the opening of the recess V and that the structure comprises a second border edge K2, being transversely bent thereto and being directed to the inner part of the recess V. The bending is preferably not exactly rectangular so that the border edges K2 run in a cone-shaped or tapered style. By doing so, the plastic tray can easily be removed from the form F during the thermo-forming (also see FIG. 2).

With respect to the desired distinct absorption of diffused light and to the enhancement of the optical quality of the tray W, it appeared that it is advantageous, if the edge surfaces K1 and K2, which are bent to each other, are formed in different sizes and that they are in particular formed so that the first edge surface K1 is smaller than the second edge surface K2. Through this, the steep stair shape shown in FIG. 1 results, having a high inclination whereby the smaller edge surfaces K1 correspondingly give a smaller reflection surface.

The tray-shaped container or the tray W preferably has the shape of a tray with several, for example 50, recesses V, being arranged in parallel to each other and extending in longitudinal direction. In this case, it can be provided that the recesses V only show a structure at their longitudinal inner surfaces F, which are oriented length-wise and which comprise in particular the groove-shaped or stair-shaped structure as shown in FIG. 1.

With FIG. 3 now the production of such a tray W will be illustrated:

The tray W is made of thermo-plastic material, in particular of polystyrene, by means of a deep-drawing method, wherein the plastic material is preferably dark colored, in particular black-colored. In the production, a plastic film or a thin plastic slide is heated and deep-drawn in a device or in a press to get the desired form or shape. The press can therefore comprise negative and positive forms as well as corresponding plunges. When using a positive form (such a shown in FIG. 2 by element "P"), the plunger (not shown) needs not to have a structure. When using a negative form, the plunger preferably also has the desired structure.

It was found out that beside a structuring of the walls, it is of advantage if at least also the bottom of the recess has a structure to avoid reflections. For this, the bottom particularly can be provided with a rough or raw structure, in that the whole surface of the deep-drawing tool is blasted/sand-blasted so that raw material gets a rough surface. The profiling of the side walls is realised during the deep-drawing by the groove structure of the molds or forms.

In FIG. 3, only the positive form P is shown as an example, having the desired groove-shaped and/or stair-shaped structure. The negative form is designed correspondingly in an inward style. Due to the structure of the molds being fitted to each other, the thermo-forming of the film or slide results in an accurate and perfect shaping. The stair structure shown here is tapered shaped, in order to allow that, at the end of the thermo-forming, the finished drawn tray W can easily be released from the forms.

Figure 4B:
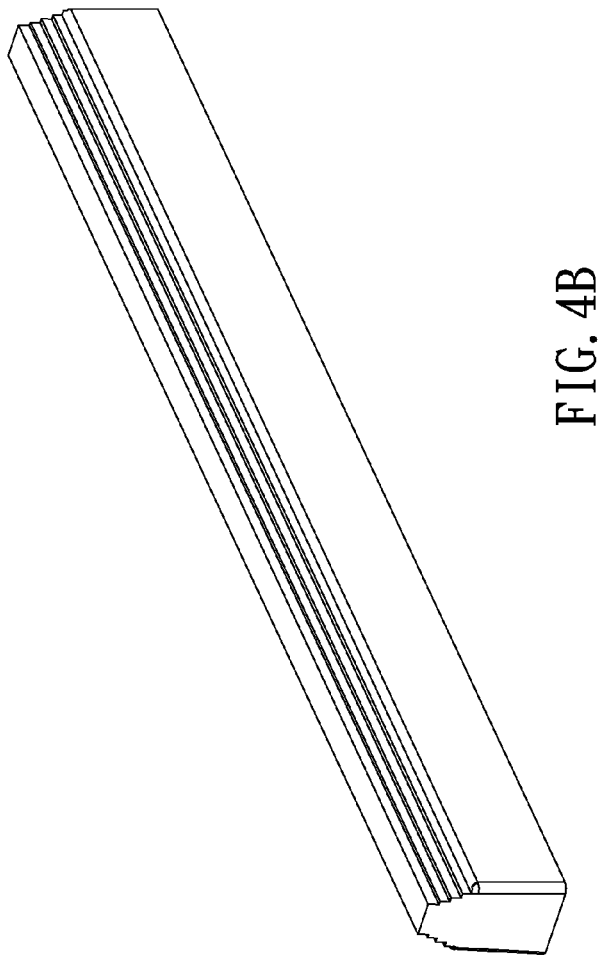
Figure 4C:
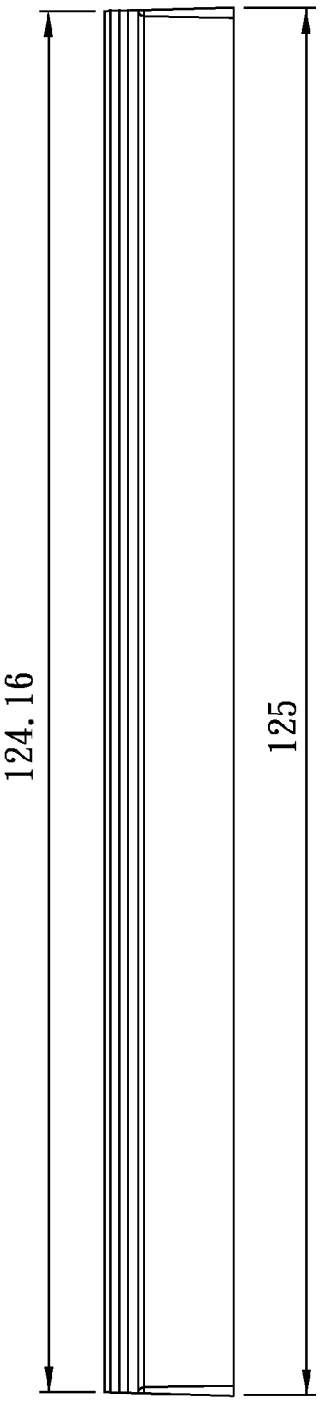
Figure 4A:
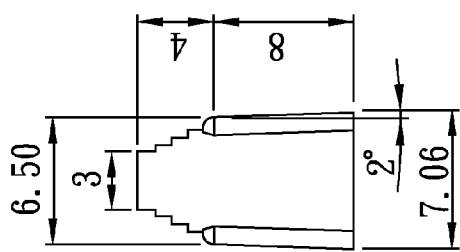

FIGS. 4a, 4b and 4c show in different views the dimensions (in mm) and the tapered form shaping of the particular recess. The recess may also be formed that it expands from its bottom to its opening by altering inclination. In particular, the recess can comprise in its bottom part (here shown on top) slanting walls than at its opening section (here shown beneath).

With the help of the described production or manufacturing device, incubation trays can be manufactured very efficiently in a thermo-forming method from plastics, preferable from dark colored polystyrene. Different forms can be used therein, comprising positive as well as negative tools with or without plunger. In order to gain as possible a constant reflection quality, it is to consider that the raw material is subject to variations as well as the temperature of the thermo-forming is having a great influence on the characteristics of the final product. For this, both parameters must be kept constantly as possible. This problem is met with the help of the specific structure of the surface of the incubation tray W. For this, the whole surface of the thermo-forming tools are sand-blasted and the side-walls (inwardly and outwardly) of the recessives in the tray W are provided with a groove-shaped profile. The applicant could find out in experiments that this in combination with a relative matt form material and with medium thermo-forming temperature, a constant and perfect reflection quality of the incubation tray could be realised for image processing.

LIST OF REFERENCE NUMERALS

| W | Tray-shaped container (incubation tray) |
|---|---|
| V | Recess(es) of the tray W |
| F | Structured inner surface of the recess V of the Tray |
| K1 | First edge surface (showing in direction of the opening of the recess |
| K2 | Second edge surface (directed to the inside of the recess |
| S | Test strip |
| S' | Fictive test strip ("ghost test strip") |
| L | Light source |
| D | Light detector or scanner |
| P | Deep-drawing or thermo-forming form (positive form) |
| M | Pattern of reaction |

The invention claimed is:

1. Tray-shaped container (W) configured for receiving solid test objects including test strips (S) to be illuminated by a light source (L) and being analyzed optically by scanning their reflections, wherein the container is configured as an incubation tray (W) comprising at least one length-wise extending recess (V) for receiving the particular test object (S), characterized in that the at least one recess (V) is cone-shaped and comprises structured inner surfaces (F) with groove-shaped or stair-shaped structure, wherein the container (W) is made of a thermo-plastic dark-colored material.

2. Tray-shaped container (W) of claim 1, characterized in that the container is designed as an incubation tray (W) for test strips (S) to be analyzed in a laboratory, wherein the incubation tray comprises several length-wise extending recesses.

3. Tray-shaped container (W) of claim 2, characterized in that the length-wise extending recesses only comprise structures at their length-wise inner surfaces (F), in particular comprise a groove-shaped and/or stair-shaped structure, being length-wise oriented.

4. Tray-shaped container (W) of claim 1, characterized in that the recesses (V) are cone-shaped forms having altering walls, wherein each of the recesses (V) expands from its bottom to its opening.

5. Tray-shaped container (W) of claim 4, characterized in that each recess (V) expands from its bottom to its opening with an altering inclination.

6. Tray-shaped container (W) of claim 1, characterized in that the stair-shaped structure comprises a first edge surface (K1), being oriented to the opening of the recess, and comprises a second edge surface (K2) being bended thereto, in particular not being bended rectangular and being oriented to the inside of the recess (V).

7. Tray-shaped container (W) of claim 6, characterized in that the edge surfaces (K1, K2) angled to each other are designed in different sizes, in particular designed such that the first edge surface (K1) is smaller than the second edge surface (K2).

8. Tray-shaped container (W) of claim 1, characterized in that also the bottom of the particular recess (V) comprises a structure, in particular a rough surface.

9. Tray-shaped container (W) of claim 1, characterized in that the container (W) is made of polystyrene.

10. Tray-shaped container (W) of claim 9, characterized in that the plastic material is black-colored.

11. Production device for thermo-forming a tray-shaped container (W) from dark colored thermo-plastic material, the container being designed as an incubation tray (W) and having the features of claim 1, characterized in that the production device comprises a positive form (P) and a cone-shaped negative form having at least one length-wise extending recess (V) for receiving solid test object (S) and having a groove-shaped or stair-shaped structure.

12. A method, comprising:
forming a tray-shaped container (W) using a thermo-forming deep drawing method using a deep-drawing tool,
wherein the tray-shaped container (W) is configured for receiving solid test objects including test strips (S) to be illuminated by a light source (L) and being analyzed optically by scanning their reflections,
wherein the container is configured as an incubation tray (W) comprising at least one length-wise extending recess (V) for receiving the particular test object (S), wherein the at least one recess (V) is cone-shaped and comprises structured inner surfaces (F) with groove-shaped or stair-shaped structure,
wherein the container (W) is made of a thermo-plastic dark-colored material.

13. The method of claim 12, wherein a surface of the deep-drawing tool is blasted.

14. A method, comprising:
thermo-forming a tray-shaped container (W) using a thermo-forming tool,
wherein the tray-shaped container (W) is configured for receiving solid test objects including test strips (S) to be illuminated by a light source (L) and being analyzed optically by scanning their reflections,
wherein the container is configured as an incubation tray (W) comprising at least one length-wise extending recess (V) for receiving the particular test object (S), characterized in that the at least one recess (V) is cone-shaped and comprises structured inner surfaces (F) with groove-shaped or stair-shaped structure,
wherein the container (W) is made of a thermo-plastic dark-colored material.

15. The method of claim 14, wherein a surface of the thermo-forming tool is blasted.

* * * * *